United States Patent
Dauvister et al.

(10) Patent No.: US 9,457,177 B2
(45) Date of Patent: Oct. 4, 2016

(54) APPARATUS FOR EXTRACTING AND RE-INJECTING ADIPOSE TISSUE

(71) Applicant: EUROMI, S.A, Verviers (BE)

(72) Inventors: Marc Dauvister, Verviers (BE); David Leleu, Verviers (BE)

(73) Assignee: EUROMI S.A., Verviers (BE)

( * ) Notice: Subject to any disclaimer, the term of this patent is extended or adjusted under 35 U.S.C. 154(b) by 0 days.

(21) Appl. No.: 14/634,309

(22) Filed: Feb. 27, 2015

(65) Prior Publication Data

US 2015/0209565 A1 Jul. 30, 2015

Related U.S. Application Data

(63) Continuation of application No. PCT/EP2013/067887, filed on Aug. 29, 2013.

(30) Foreign Application Priority Data

Aug. 29, 2012 (EP) .................................... 12182191

(51) Int. Cl.
*A61M 1/00* (2006.01)
*A61M 37/00* (2006.01)
(Continued)

(52) U.S. Cl.
CPC .... *A61M 37/0092* (2013.01); *A61B 17/32002* (2013.01); *A61B 17/320068* (2013.01);
(Continued)

(58) Field of Classification Search
CPC .................. A61B 17/00234; A61B 17/32002; A61B 17/320068; A61B 17/3476; A61B 2017/0023; A61B 2017/0046; A61B 2017/00544; A61B 2017/00561; A61B 2017/00792; A61B 2017/00969; A61B 2017/320024; A61B 2217/005; A61B 2017/320028; A61M 1/0001; A61M 1/0023; A61M 1/0039; A61M 2037/0007; A61M 2202/0413; A61M 2202/08; A61M 2205/7545; A61M 37/0092; A61M 39/223; A61M 1/0058; A61M 2202/0021; A61M 2205/75
See application file for complete search history.

(56) References Cited

U.S. PATENT DOCUMENTS 2,032,723 A * 3/1936 Schweser ................ A61M 5/31
604/117
4,253,501 A * 3/1981 Ogle ..................... A61J 1/2096
128/DIG. 12
(Continued)

FOREIGN PATENT DOCUMENTS

WO 9844966 10/1998
WO 2004067065 8/2004
(Continued)

OTHER PUBLICATIONS

International Search Report, issued by the International Searching Authority in connection with International patent application No. PCT/EP2013/067887, mailed on Nov. 7, 2013, 2 pages.
(Continued)

*Primary Examiner* — Adam Marcetich
(74) *Attorney, Agent, or Firm* — Hanley, Flight & Zimmerman, LLC

(57) ABSTRACT

Example kits of parts, apparatus and methods for liposuction and lipofilling of adipose tissue are disclosed. An example kit includes an extraction unit comprising a liposuction device having a cannula coupled to a handpiece, which imparts movement to an inlet end of the cannula. The example kit includes a separation unit, a re-injection unit, a vacuum pump, a re-injection pump, and tubing for connecting the elements of the kit of parts to form an apparatus for liposuction and lipofilling of adipose tissue. The example handpiece imparts to the inlet end of the cannula a vibrational movement comprising a first, linear component and a second, orbital component. The example kit also includes a three-way valve having an aspiration position to bring a retentate volume of the separation unit in communication with the re-injection pump, and an injection position to bring the re-injection pump in communication with the lipofilling device.

19 Claims, 5 Drawing Sheets

(51) Int. Cl.
*A61M 39/22* (2006.01)
*A61M 25/00* (2006.01)
*A61B 17/34* (2006.01)
*A61B 17/32* (2006.01)
*A61B 17/00* (2006.01)

(52) U.S. Cl.
CPC ........ *A61B17/3476* (2013.01); *A61M 1/0001* (2013.01); *A61M 1/0039* (2013.01); *A61M 39/223* (2013.01); A61B 17/00234 (2013.01); A61B 2017/0023 (2013.01); A61B 2017/0046 (2013.01); A61B 2017/00544 (2013.01); A61B 2017/00561 (2013.01); A61B 2017/00792 (2013.01); A61B 2017/00969 (2013.01); A61B 2017/320024 (2013.01); A61B 2017/320028 (2013.01); A61B 2217/005 (2013.01); A61M 1/0023 (2013.01); A61M 1/0058 (2013.01); A61M 2037/0007 (2013.01); A61M 2202/0021 (2013.01); A61M 2202/0413 (2013.01); A61M 2202/08 (2013.01); A61M 2205/075 (2013.01); A61M 2205/7545 (2013.01)

(56) References Cited

U.S. PATENT DOCUMENTS

| | | | | |
|---|---|---|---|---|
| 4,536,180 | A | | 8/1985 | Johnson |
| 5,055,198 | A | * | 10/1991 | Shettigar ............... A61M 1/02 210/104 |
| 5,439,452 | A | * | 8/1995 | McCarty ............ A61M 39/223 137/625.22 |
| 5,814,044 | A | * | 9/1998 | Hooven ........... A61B 17/32002 604/21 |
| 5,911,700 | A | | 6/1999 | Mozsary et al. |
| 6,336,925 | B1 | * | 1/2002 | Malak .................. A61M 1/008 604/22 |
| 6,494,876 | B1 | | 12/2002 | Fowler et al. |
| 8,172,832 | B1 | * | 5/2012 | Gonzalez ............ A61M 1/0001 604/317 |
| 2003/0161816 | A1 | * | 8/2003 | Fraser .................. C12N 5/0667 424/93.7 |
| 2003/0187383 | A1 | * | 10/2003 | Weber .............. A61B 17/32002 604/22 |
| 2004/0034340 | A1 | * | 2/2004 | Biscup .................. A61B 18/20 606/1 |
| 2006/0224144 | A1 | | 10/2006 | Lee |
| 2007/0233131 | A1 | * | 10/2007 | Song ................... A61B 17/1671 606/79 |
| 2008/0021487 | A1 | * | 1/2008 | Heisler ............ A61B 17/32002 606/170 |
| 2009/0181104 | A1 | | 7/2009 | Rigotti et al. |
| 2009/0287190 | A1 | * | 11/2009 | Shippert ............. A61M 1/0001 604/542 |
| 2009/0304643 | A1 | * | 12/2009 | Khurgel ........... A61K 47/48776 424/93.7 |
| 2013/0012921 | A1 | * | 1/2013 | Pustilnik ................. A61M 1/00 604/518 |
| 2013/0131655 | A1 | | 5/2013 | Rigotti et al. |

FOREIGN PATENT DOCUMENTS

| | | |
|---|---|---|
| WO | 2009079431 | 6/2009 |
| WO | 2011146924 | 11/2011 |
| WO | 2013107898 | 7/2013 |

OTHER PUBLICATIONS

International Preliminary Report on Patentability, issued by the International Searching Authority in connection with International patent application No. PCT/EP2013/067887, mailed on Aug. 14, 2014, 13 pages.

Wikipedia, "Adipose Tissue," retrieved from [URL: https://en.wikipedia.org/wiki/Adipose_tissue] on Feb. 19, 2015, 13 pages.

Traktuev et al., "A Population of Multipotent CD34-Positive Adipose Stromal Cells Share Pericyte and Mesenchymal Surface Markers, Reside in a Periendothelial Location, and Stabilize Endothelial Networks," Circulation Research, Jan. 4, 2008, vol. 102(1): 77-85. Published online before print Oct. 25, 2007, retrieved from [URL: http://circres.ahajournals.org/content/102/1/77.long] on Feb. 19, 2015, 15 pages.

Euromi, "Lipomatic 3," retrieved from [URL: https://www.euromi.com/en/component/virtuemart/lipomatic/lipomatic-3-detail?Itemid=0] on Feb. 19, 2015, 2 pages.

* cited by examiner

APPARATUS FOR EXTRACTING AND RE-INJECTING ADIPOSE TISSUE

RELATED APPLICATIONS

This patent arises from a continuation of International Patent Application Serial No. PCT/EP2013/067887, filed Aug. 29, 2013, which claims priority to European Patent Application 12182191.2, filed on Aug. 29, 2012, both of which are hereby incorporated herein by reference in their entireties.

TECHNICAL FIELD

The present disclosure concerns a kit of parts, an apparatus and methods for extracting adipose tissue from a location of a patient and re-injecting adipose cells from said adipose tissue into another location of said patient (or of another patient).

BACKGROUND

"Adipose tissue" or (body) "fat" is loose connective tissue composed mostly of adipocytes or "fat cells". In addition to adipocytes, adipose tissue contains the stromal vascular fraction (SVF) of cells including preadipocytes, fibroblasts, vascular endothelial cells and a variety of immune cells (cf. https://en.wikipedia.org/wiki/Adipose_tissue). Far from being inert, it has been established that adipose tissue can produce hormones, and is an abundant source of CD34+ cells (cf. Traktuev et al., Circ Res. 2008 Jan. 4; 102(1): 77-85. Epub 2007 Oct. 25, also available in http://www.ncbi.nlm.nih.gov/pubmed/17967785). CD34+ cells are a mixture of stem cells, progenitors, and white blood cells of various degrees of maturity.

Excess adipose tissue can be removed from a specific location of a body by liposuction. In liposuction, a hollow cannula comprising an opening at or close to its free end, is inserted into the region of the body to be treated through a small incision in the skin. Fat cells are aspirated through the lumen of the cannula which is connected to a vacuum source and thus driven into a container. Liposuction can be applied for therapeutic reasons to treat obesity, which is an excess of adipose tissue, or it can be applied for cosmetic reasons to improve one's figure.

As improving one's figure is not restricted to removing adipose cells from locations where it is considered they are present in excess, but may also comprise giving volume to locations of the body considered as volume deficient, it has rapidly been proposed to re-inject a fraction of the adipose tissue extracted from one location of the body in excess of body fat, into another location deficient in adipose tissue, like e.g., lips, cheeks, breast. This solution is appealing since there is no risk of rejection of its own cells by the patient. The extraction of adipose tissue is often referred to as "liposuction", the re-injection as "lipofilling" and, in cosmetic applications, a liposuction followed by a lipofilling is often artistically referred to as "liposculpture." Unfortunately, it has been observed that, when the "sculptural" result obtained at the end of a lipofilling operation could be fully satisfactory, with an increase in volume of those parts of the body which were considered as in need, said result rapidly decayed with time with a substantial loss of volume of the order of 50 to 60% after a few days only. Lipofilling effects were declared to be transient only. Two solutions were proposed. First, it was proposed to increase the lipofilling volume during the operation such that, the time dependent loss of volume would eventually yield the desired volume. It is clear that such solution has two major inconveniences: the "sculptural" effect after the operation is certainly not at the level of expectation of the patient, and it is difficult to establish with certainty the percentage of volume loss with time. The second solution which was proposed, and is still widely in use today, is to store the extracted adipose tissue and to re-inject it in small doses in several lipofilling interventions spread in time, like the repetitive brush strokes given by a painter to give depth to its composition. But if the art comparison in the term "liposculpture" is appealing, it is clear that for the patient it is very inconvenient to undergo a series of lipofilling interventions, which are rather intrusive, long (ca 0.5-1.5 h), carried out under anaesthesia (at least local), and which can form an hematoma at the re-injection point(s) for several days each time. Furthermore; the risks of degradation or infection of the adipose cells increase with storing time.

It is believed with sufficient certainty, that the reason for the transient effect of lipofilling is due to the fact that adipose tissue is extracted by liposuction in the form of lumps or agglomerates of adipocytes and other cells, as illustrated in FIG. 3(a), left hand side. As adipose tissue is re-injected in the body, vascularization of the cells begins. If the adipose cells present at the periphery of the agglomerate are easily vascularized, this is not the case of the cells present in the core of the agglomerate. The core cells rapidly die due to necrosis and the thus hollow agglomerate collapses and flattens, thus explaining the loss of volume observed with time after a lipofilling operation (cf. FIG. 3(a), right hand side, shaded cells indicate necrosis).

Re-injection of a fraction of the adipose tissue extracted by liposuction is drawing more and more attention in therapeutical applications, in particular for the recovery and re-injection of regenerative cells abundantly present in adipose tissue, such as for examples stem cells, in particular CD34+ cells, sometimes referred to as adipose derived stem cells (ADSC). If adipose cells necrosis is inconvenient in liposculpture for cosmetic applications, it is a major drawback for the collection and re-injection of specific cells like stem cells.

A liposuction device comprises a long, hollow cannula coupled to a handpiece, with one or more openings at or adjacent to the tip end thereof. The lumen is in fluid communication with an extracting tube and with a vacuum pump for driving the extraction of the adipose tissue, when the tip end of the cannula is inserted within the adipose tissue to be treated. Liposuction devices may or may not have a power assisted handpiece, suitable for imparting a given movement, generally a reciprocal movement, to the tip of the cannula.

U.S. Pat. No. 4,536,180 mentions a manual (i.e., non-powered) liposuction device, wherein no additional movement is imparted to the cannula by a power source. U.S. Pat. No. 6,494,876 mentions a liposuction device wherein a cannula is attached to a power assisted handpiece which reciprocates the cannula back and forth along the longitudinal axis of the cannula at a frequency of 400 to 800 cycles per min (=6.7-13.3 Hz). Similarly, U.S. Pat. No. 5,911,700 mentions a powered liposuction device reciprocating back and forth the cannula along its longitudinal axis at an amplitude of 1 to 10 mm. International Patent Publication WO9844966 mentions a powered liposuction device imparting to the cannula a combined movement of longitudinal back and forth reciprocation at a frequency of 10 to 500 Hz and a movement of nutation (vibrating and orbiting movements combination of the tip end of the cannula about the longitudinal axis thereof at rest). None of the foregoing disclosures addresses survival of the extracted adipose tissue thus extracted. Of course, there are many more disclosures of liposuction devices, but few address survival of the extracted adipose tissue because extracted adipose tissue is generally simply destroyed or disposed of after extraction.

International Patent Publication WO2011146924 describes a power assisted liposuction device for extracting adipose cells generating ultrasonic energy transmitted to the cannula. The ultrasonic frequency, f, is restricted between 35 and 45 kHz because, according to the authors, all ultrasonic frequencies are not appropriate for cell survival, as it seems to be the case for Lysonix® liposuction device discussed therein. WO2011146924 teaches that the adipose tissue thus extracted can be filtered to remove the larger material and the filtrate contains the adipose derived stem cells (AD-SC's). The removal of larger material strongly suggests that agglomerates of adipocyte cells are extracted by liposuction and discarded by the filtration operation, resulting in a great loss of potential ADSC's present in the discarded adipocyte agglomerates.

U.S. Pat. No. 5,911,700 describes a power assisted liposuction device for extracting adipose cells using a powered liposuction device. In one embodiment, a filtering means is interposed between the liposuction device and a vacuum pump to separate a selected portion of adipose tissue from undesired material. The pump can then be reversed to pressurize the selected portion of adipose tissue and drive it back towards the liposuction device used this time as lipofilling device. It is clear that such description has never been implemented because it does not make sense to use a powered handpiece to inject tissues into a part of a body requiring extreme precision, the movement of the cannula preventing any targeted injection of tissues. Furthermore, the cannulas used in lipofilling are different from the ones used for liposuction, the former being generally thinner and, in particular, comprising a single outlet at the tip of the cannula, whilst liposuction devices generally comprise a multitude of inlet windows at the tip of the cannula. Injecting tissues with a cannula comprising several outlets does not permit any precise injection work.

SUMMARY

The present disclosure is defined in the appended independent claims. Further examples are defined in the dependent claims. The present disclosure details an apparatus that allows the enhancement of the survival of injected adipose cells obtained from liposuction. In some disclosed examples, an apparatus allows the extraction of adipose tissue, separation of a portion of said tissue to remove undesirable material, and re-injection of the thus separated portion of adipose tissue. The example apparatus of the present disclosure yields a higher survival rate of re-injected cells than hitherto achieved, and permits a substantial shortening of the operation(s) required for refilling a location of a body. This and other advantages of the present disclosure are presented herein.

In particular, one example of the present disclosure concerns an example kit of parts for an apparatus for liposuction and lipofilling of adipose tissue, said kit of parts comprising an extraction unit comprising a liposuction device that has a substantially linear, hollow, elongated cannula with an inner lumen extending along a longitudinal axis of symmetry, X, first inlet end, provided with one or several openings for drawing adipose tissue into said lumen, to a second, outlet end, located at the opposite end of the elongated body. In such example, said cannula is coupled by means of fixing means to a powered handpiece suitable for imparting a given movement to the inlet end of the cannula. The example kit of parts also includes a separation unit, comprising a vessel, provided with separation means, for separating a selected portion of adipose tissue from liquids and other undesired solids. The example kit of parts also includes a re-injection unit comprising a lipofilling unit comprising a cannula as defined above, coupled to a handpiece. The example kit of parts also includes a vacuum pump suitable for creating a vacuum in the lumen of the cannula of the liposuction device sufficient for drawing adipose tissue out of a location of a body. The example kit of parts also includes a re-injection pump suitable for driving said selected portion of adipose tissue from the vessel to the lumen of the cannula of the lipofilling device under sufficient pressure for injecting said selected portion of adipose tissue into a location of a body. In addition, the example kit of parts also includes tubing for connecting the various elements of the kit of parts together such as to form an apparatus for liposuction and lipofilling of adipose tissue. In this example, the powered handpiece of the liposuction device is suitable for imparting to the inlet end of the cannula a movement comprising a first, linear component of a back and forth reciprocal movement along the longitudinal axis, X, at a frequency of 10 to 500 Hz and a second, orbital component about the longitudinal axis, X, wherein the movement can be referred to as a nutational movement.

In some examples, the amplitude of the longitudinal component of the vibrational movement of the inlet end of the liposuction device's cannula is not more than 10 mm, and in some examples, between 2 and 9 mm. The orbital component about the longitudinal axis, X, of the inlet end vibrational movement is elliptical, defined by a major diameter, D, and a minor diameter, d, the major diameter, D, being comprised between 1 and 20 mm, and in some examples, between 2 and 10 mm.

The powered handpiece of the liposuction device is powered pneumatically, in some examples. Also, in some examples, the powered handpiece comprises an inner channel extending along a longitudinal axis from a first, upstream end to a second, opposite, downstream end of the handpiece, and that the fixing means of the cannula of the liposuction device is located on the elongated body between the inlet and the outlet ends, for removably and solidly fixing the cannula to the said handpiece at the level of the upstream end of the inner channel thereof, such that the portion comprised between the fixing means and the cannula outlet extends through said inner channel and such that the cannula outlet is located outside the handpiece's inner channel.

The vacuum pump, in some examples, is distinct from the re-injection pump, which in some examples is a piston pump.

In some examples, the separating means of the separating unit (B) comprise a filter defining a filtrate volume of the vessel, for receiving the filtrate formed by the liquids and other undesired solids, and a retentate volume of the vessel for holding the selected portion of adipose tissue. In some examples, the vessel of the separating unit comprises a first inlet opening, for receiving extracted adipose tissue from the liposuction device, a second, feeding opening for feeding a portion of the adipose tissue stored therein, both inlet opening and feeding opening being located in the retentate volume of the vessel, a third, discharge opening located at the lowest point of the filtrate volume of the vessel when in use, for discharging any excess material therefrom, and a fourth opening for connecting the interior of the vessel to a vacuum pump.

The present disclosure also concerns an apparatus for liposuction and lipofilling of adipose tissue comprising all the elements of the kit of parts defined supra, wherein: the outlet of the liposuction device cannula is in fluid communication through a liposuction tube with a retentate volume of the vessel for holding the selected portion of adipose tissue after separation by the separating means, said retentate volume being located within the vessel, and in some examples, upstream from the separating means. In some examples, the vessel of the separating unit is connected through a vacuum pipe to the vacuum pump, the latter thus being also in fluid communication with the inlet of the liposuction device cannula through the liposuction tube and the lumen of the cannula. Also, in some examples, the lipofilling device is in fluid communication with a volume of the vessel for holding the selected portion of adipose tissue after separation by the separating means through a feeding tube, and with the re-injection pump.

In some examples, the re-injection pump of the apparatus according to the present disclosure is a piston pump. In some examples, the apparatus further comprises a three-way valve having: a first, aspiration position, wherein the retentate volume of the vessel of the separation unit for holding the selected portion of adipose tissue is in fluid communication with said piston pump, and a second, injection position, wherein the piston pump is in fluid communication with the lipofilling device.

The apparatus according to the present disclosure can be used in example methods disclosed herein. One example method includes extracting adipose tissue from a location of a body with the liposuction device and driving the adipose tissue to the vessel of the separation unit and separating a selected portion of adipose cells from liquids such as blood and other liquids. The example method also includes drawing selected portion of adipose tissue from the vessel and feeding it under pressure to the lipofilling device, and re-injecting the selected portion of adipose tissue with the lipofilling device into another location of the body. The example methods applied with the example apparatus of the present disclosure can be a cosmetic, liposculpture method. Alternatively, or concomitantly, it can be a therapeutic method wherein the selected portion of adipose tissue comprises a concentration of Adipose Derived Stem Cell (ADSC) for stimulation of regeneration of an organ or muscle of a body. With the example apparatus of the present disclosure, the viability of ADSC of the selected portion of adipose tissue determined by Fluorescent Activated Cell Sorting (FACS) flow Cytometry can reach an average value of at least 78%, and in some examples at least 82%, at least 85%, and at least 88%. With an apparatus according to the example present disclosure, extraction of adipose tissue and re-injection of a selected portion of adipose tissue can advantageously be carried out within a single operative session.

BRIEF DESCRIPTION OF THE FIGURES

For a fuller understanding of the nature of the present disclosure, reference is made to the following detailed description taken in conjunction with the accompanying drawings in which.

DETAILED DESCRIPTION

The present disclosure concerns an example kit of parts and an example apparatus for liposuction and lipofilling of adipose tissue. The apparatus of the present disclosure comprises all the elements of the kit of parts, assembled together such as to bring in fluid communication the various elements with one another in an appropriate way. In order to avoid unnecessary repetitions, the discussion in the present section focuses on the apparatus in its assembled form and not on the kit of parts which comprises the same elements in a dismantled form. It is clear, however, that all the features discussed with reference to the individual elements of the apparatus apply mutatis mutandis to the elements of the kit of parts.

In some examples, the example apparatus comprises (A) an extraction unit for extracting the adipose tissue, (B) a separation unit to isolate the adipose cells to be re-injected, and (C) a re-injection unit for re-injecting the isolated adipose cells ensuring sterile conditions of the surfaces entering in contact with extracted cells throughout the apparatus. The example liposuction unit of the present disclosure is particularly suitable for securing healthy adipose cells which are rich in viable regenerative cells.

Figure 1:
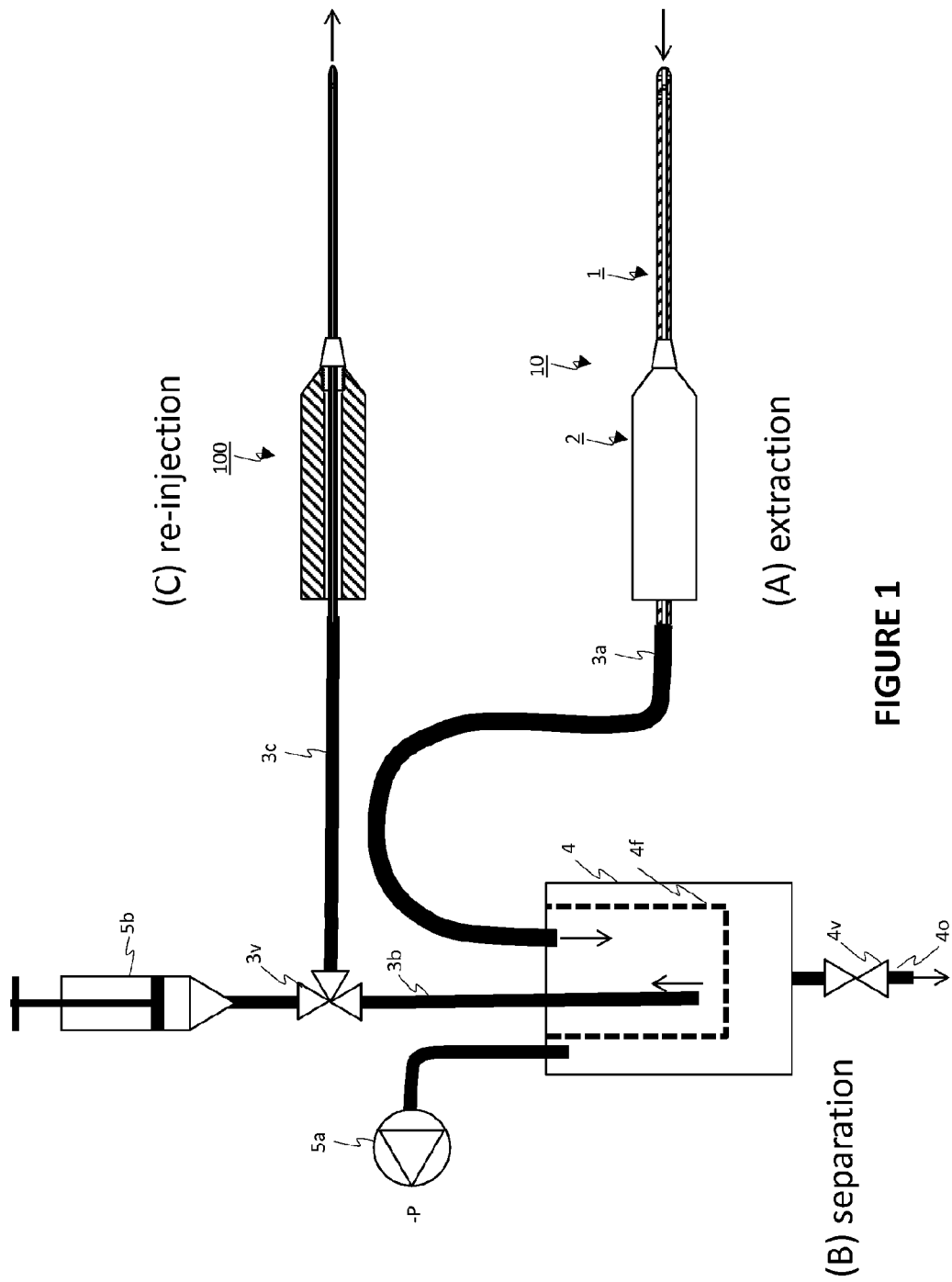
FIG. 1: shows an example liposuction and re-injection apparatus according to the present disclosure.

As illustrated in FIG. 1, an apparatus according to the present disclosure comprises three main units: (A) then extraction unit, (B) the separation unit, and (C) the re-injection unit. Because of the transient nature of the lipofilling effect obtained up to date due to necrosis of a large proportion of adipose tissue extracted with conventional liposuction devices and re-injection of a fraction thereof in another location of the body, requiring that the lipofilling operation be carried out by several operations spread in time, an apparatus comprising both liposuction device (10) and lipofilling device (100) made little sense. Indeed, it was not current practice to carry out a lipofilling operation in the same session as the liposuction operation. The adipose tissue extracted with the liposuction device was generally stored in a container (4) at low temperature until further use on another or several other days. The thus stored material was generally further treated by sedimentation, filtration, centrifugation and the like, for separating a selected portion of the adipose tissue from undesired residue, like blood or any solution injected into the body prior to the liposuction operation in order to facilitate extraction of adipose cells.

With an apparatus according to the present disclosure, it is possible to ensure a substantially higher viability of the adipose cells, thanks to the specific vibrational movement of the cannula which will be discussed more in detail below. The lipofilling effect is now substantially permanent, and it is now possible to re-inject the entire desired volume of selected adipose tissue into a location of a body in one single session, which can be immediately after liposuction. The two operations of liposuction and lipofilling can thus be separated only by the time required for separating a selected portion of the adipose tissue from undesired residue. This results in an enormous progress in the field of liposculpture, both cosmetic and therapeutic, wherein the selected portion of adipose tissue comprises adipose derived stem cells (ADSC) for regenerative applications.

(A) Extraction Unit

Figure 4:
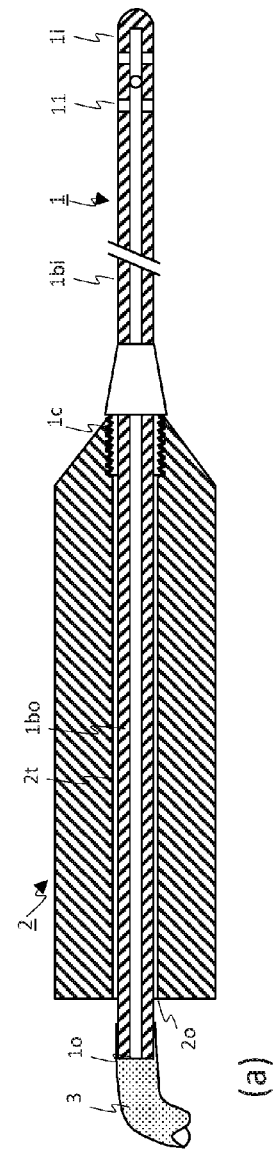
FIG. 4: shows two example embodiments of liposuction devices with cannulas according to the present disclosure.
Figure 4:
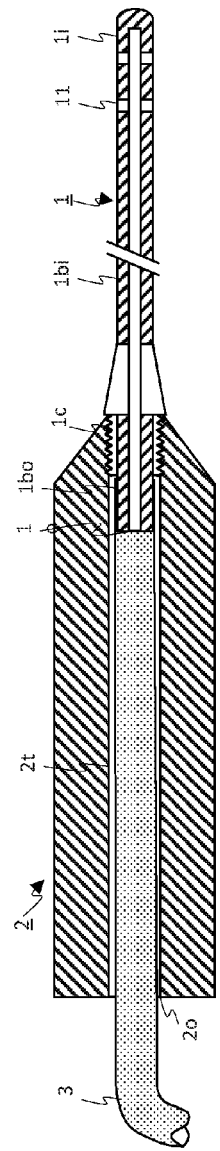
Figure 5:
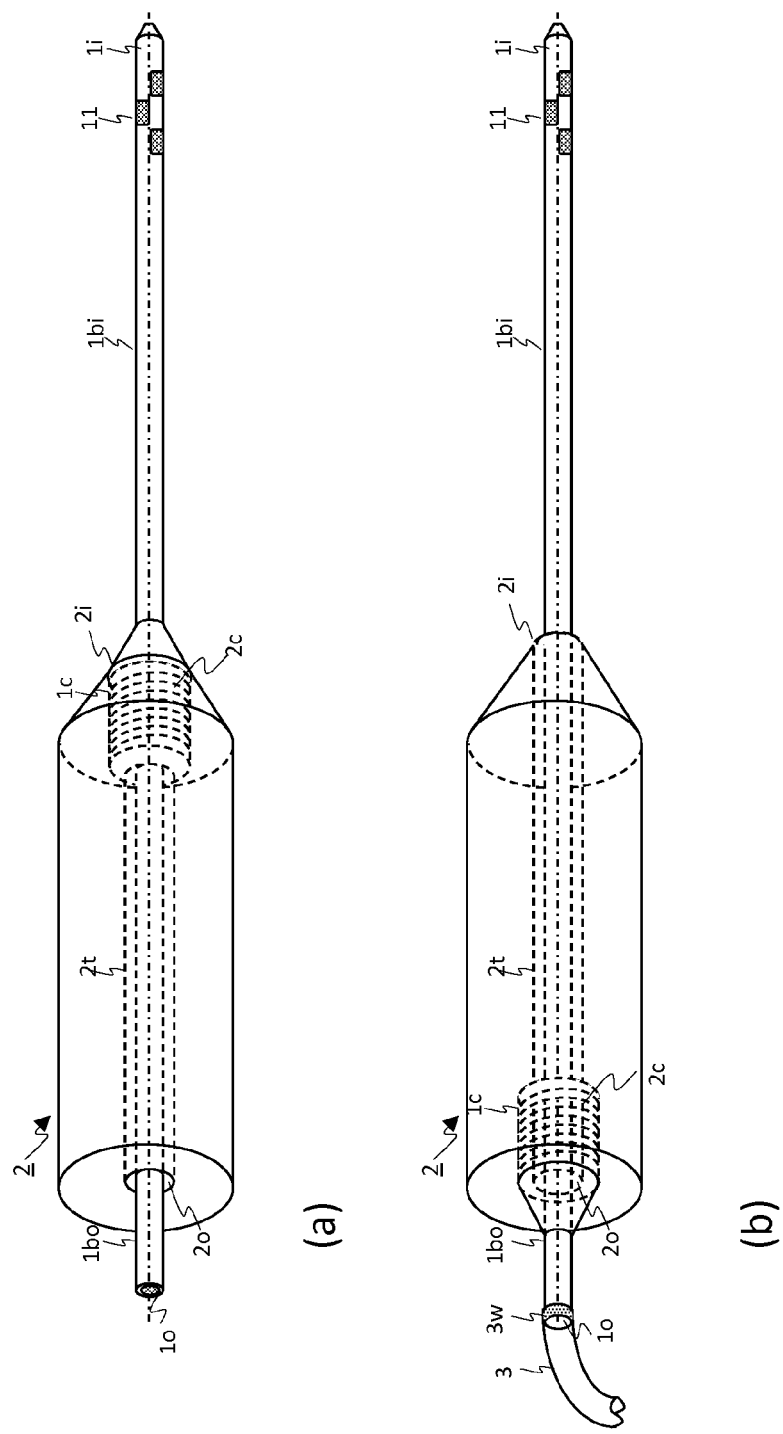
FIG. 5: shows two example embodiments of a liposuction device with cannula.
Figure 6:
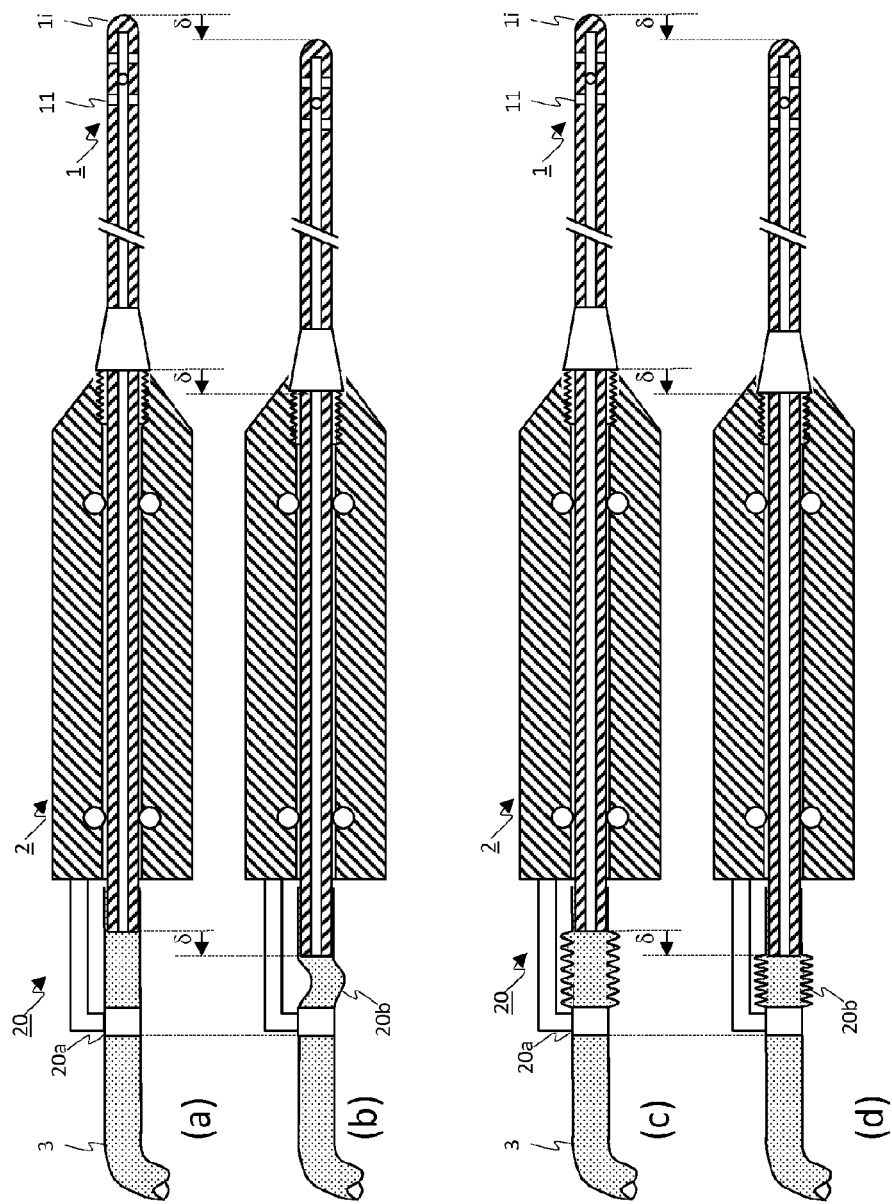
FIG. 6: shows two example embodiments of a liposuction devices comprising means for absorbing the vibrational movement of the cannula.

The extraction unit (A) comprises a liposuction device (10) connected to a vacuum pump (5a). As illustrated in FIGS. 4-6, the liposuction device comprises a substantially linear, hollow, elongated cannula (1) with an inner lumen extending along a longitudinal axis, X, from a first inlet end (1i), provided with one or several openings (11) for drawing adipose tissue into said lumen, to a second, outlet end (1o), located at the opposite end of the elongated body, said cannula being coupled by means of fixing means (1c) to a powered handpiece (2). The powered handpiece (2) is suitable for imparting to the inlet end (1i) of the cannula a vibrational movement comprising a first, linear component of a back and forth reciprocal movement along the longitudinal axis, X, (δ, FIG. 6) at a frequency, f, of 1 to 500 Hz. In some examples the frequency is between 10 and 50 Hz, and in some examples between 15 and 20 Hz. FIG. 6 shows structure 20 between the handpiece (2) and the vacuum tube (3) to absorb the linear vibrational movement (6) therebetween, which includes element 20a fixed to the vacuum tube (3) and flexible means 20b (including, e.g., bellows in FIGS. 6c and 6d) that deforms when the cannula oscillates in the longitudinal direction (δ).

Figure 2:
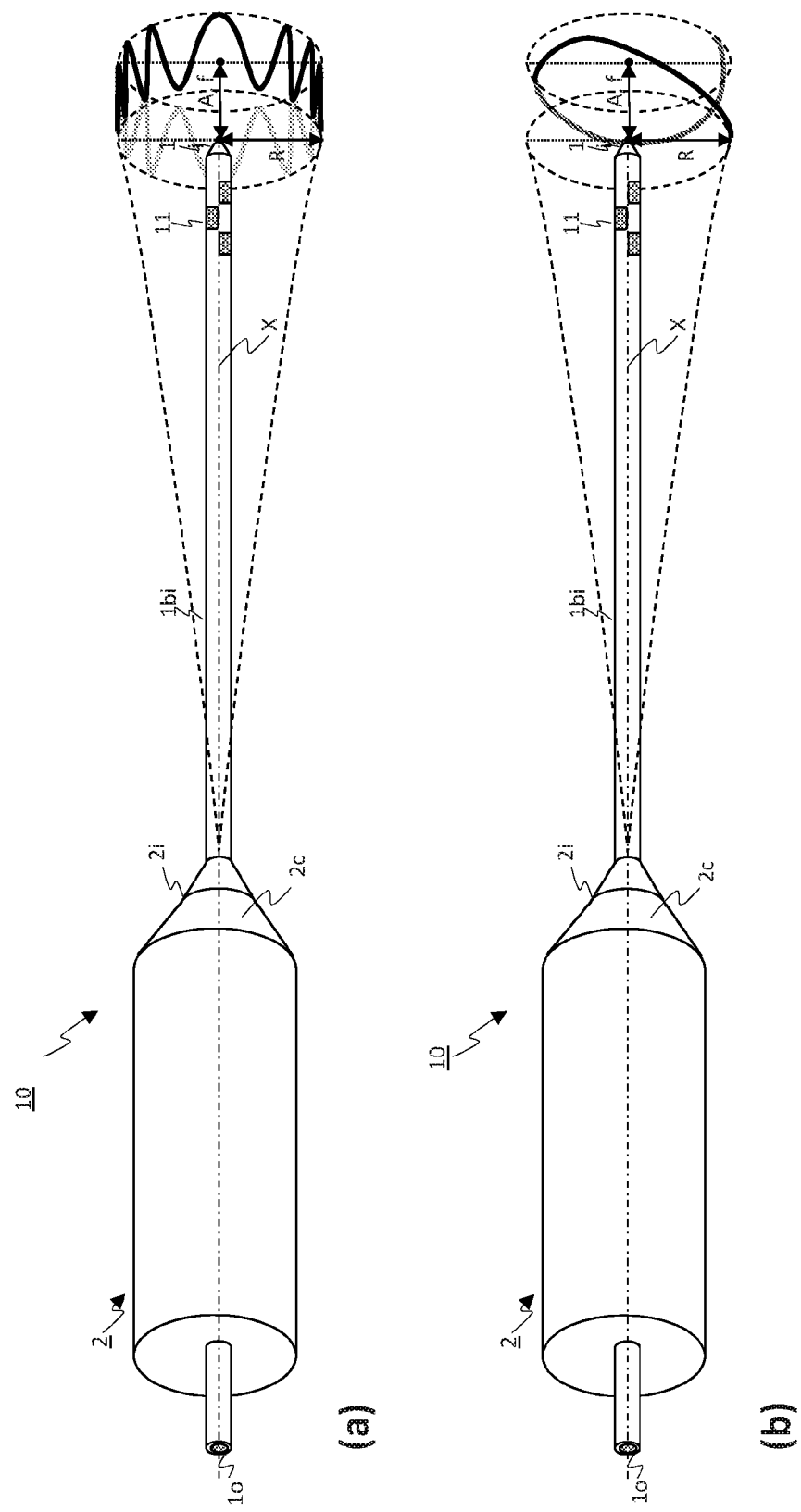
FIG. 2: shows an example liposuction device and a vibrational movement of the cannula tip end comprising a longitudinal, reciprocal component and of an orbital component.

The vibrational movement also comprises and a second, orbital component about the longitudinal axis, X (cf. FIG. 2). The orbital component of the vibrational movement is usually substantially elliptical. The frequency and dimensions of the elliptical orbit, defined by its major diameter, D, and minor diameter, d, depend on the pressure applied onto the cannula and at what point thereof. The cannula's inlet end has a given orbital component when the cannula is free of any constraints, other than being fixed to the handpiece. When the cannula is inserted into a body part through an incision, the cannula is pressed by the tissues surrounding it, and the orbital component varies both in dimensions and in frequency like a guitar string being pressed by a player's fingers will change the vibrational frequency of the string. Special imaging has shown that the cannula's orbital component is maintained, and even often accentuated when the cannula is inserted into a body part. If the frequency of the longitudinal component of the movement is higher than the frequency of orbital revolution, the cannula's tip will follow a trajectory as represented in FIG. 2(a). If it is lower, than it will follow a trajectory as illustrated in FIG. 2(b).

An example of liposuction device (10) suitable for the present disclosure is described in International Patent Publication WO9844966 and U.S. Pat. No. 6,336,925, the content of each being herein incorporated by reference. The movement of the cannula in such liposuction device is a nutation movement comprising an orbital component about the longitudinal axis, X, and a translation component according to the longitudinal axis of the cannula. The translation component, in some examples, has an amplitude (i.e., end-to-end distance ran by the inlet of the cannula during one stroke in one direction along the longitudinal axis, X) less than 10 mm, and in some examples greater than 1 mm. In some examples, the amplitude of the translation component is comprised between 2 and 9 mm, and in some examples, between 5 and 8 mm. The major diameter, D, of the elliptical orbital component, followed by the cannula's tip when orbiting about the longitudinal axis, X, is comprised, in some examples, between 1 and 20 mm, and in some examples, between 2 and 10 mm. The characteristics of the vibrational movement of the tip of the cannula can be controlled by a combination of at least the following parameters:

Moment of torsion of the cannula, dependent on the length, diameter, cross-sectional geometry, wall thickness and material of the cannula, Smoothness, amplitude and frequency of the reciprocal driving along the longitudinal axis of the cannula, which must avoid shocks at the end of each stroke, which would disrupt the conditions for an orbital component of the vibrational movement of the cannula's tip (a pneumatic driving system as described in WO9844966 may be used in some examples as it smoothens the reciprocal movement of the cannula at its ends), Clearance of the cannula at the inlet end of the handpiece, which can control the extent the vibrational component of the cannula movement can develop in the radial direction, Mechanical pressure on part of the cannula, e.g., by surrounding tissues when introduced into a body part (note that the vibrational movement of the cannula defined in the appended claims refers to an unconstrained cannula, apart from its fixing point to the handpiece).

Figure 3:
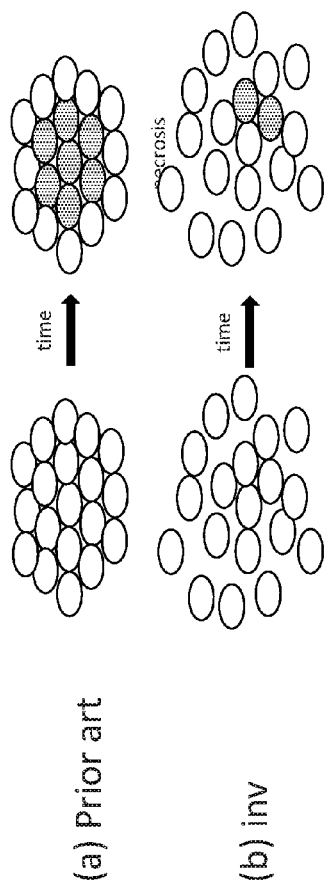
FIG. 3: shows the structure of extracted adipose tissue as extracted and after some days, extracted (a) with non-powered liposuction device and (b) with a liposuction device as defined in the present disclosure (shaded cells indicate necrosis thereof).

The driving of the powered handpiece is, in some examples, pneumatical as it allows a smooth reciprocal-orbital movement of the cannula tip, without any impact or shock. An example pneumatic drive for imparting a reciprocal-orbital movement to the tip of the cannula is described in International Patent Publication WO2013107898, with reference to FIG. 3 thereof (cf. p.11ff of WO2013107898) and in European Patent EP0971754 with reference to FIGS. 6 to 8. The description of the pneumatic drive in WO2013107898 and EP0971754 is herein included by reference.

It was observed that, when adipose tissue extracted with a manual or other powered liposuction devices were collected in the form of lumps of a rather large number of adipose cells as illustrated schematically in FIG. 3(a), left hand side, the adipose tissue extracted with a liposuction device as defined supra were in the form of substantially smaller lumps and of individual cells as illustrated in FIG. 3(b), left hand side. Without wishing to be bound by any theory, it is believed that the relatively low frequency reciprocal-orbital movement of the cannula tip contributes to dislocating the large lumps of adipose tissue without severing through cells and blood vessels, and forming instead an emulsion of adipose cells (note that a solution (e.g., Klein solution) is generally injected prior to liposuction, including an anaesthetic and for facilitating extraction of the adipose tissue). As discussed supra and illustrated in FIG. 3(a), right hand side, the adipose cells present in the core of large lumps cannot be re-vascularized properly after re-injection into a body, leading rapidly to necrosis thereof (cf. shaded cells in FIG. 3(a)), rapidly (in a few days) yielding hollow lumps of adipose cells which then collapse. This is the supposed mechanism of the transient effect of lipofilling described in the background art. By contrast, because all large lumps are dislocated when extracted with a liposuction device as defined in the present disclosure, re-vascularization of the adipose cells is much more complete and only few cells are affected by necrosis. This leads to the advantageous permanent effect of lipofilling observed with the example apparatus of the present disclosure. Tests, which will be presented in continuation, revealed that adipose derived stem cells (ADSC) extracted with a liposuction device as defined in the present invention, yielded an average viability of 90% against only 72% with ADSC extracted with a manual liposuction device.

(B) Separation Unit

Since the time delay between liposuction and lipofilling operations is technically dependent only on the time for separating a selected portion of adipose tissue thus extracted from undesired residue, it is advantageous to shorten such separation step as much as possible. Another issue, not as critical in case of simple liposuction operations, wherein the extracted adipose tissue is then disposed of, is to maintain sterile conditions throughout the apparatus parts entering in contact with adipose cells during the whole time between extraction of the adipose tissue and re-injection of a selected portion thereof. It is clear that in the prior art systems, wherein extraction and re-injection were separated in time by several days or weeks, the risks of contamination of the selected portion of adipose tissue increased with storage time and with handling required for such storage and repeated lipofilling operations. In the present disclosure, all elements of the apparatus can be maintained hermetically sealed in sterile conditions during the whole duration of the extraction and re-injection operations. In this sense, in some example embodiments, the separation unit (B) comprises a vessel (4) and integrated therein a separation means (4f). The vessel may be a beaker provided with a lid sealed thereon by welding or gluing. The separation means, in some examples, include a filter of desired mesh size as illustrated in FIG. 1, defining a first, retentate volume, upstream from the filter (4f) for holding the selected portion of adipose tissue, and a second, filtrate volume, for receiving the filtrate consisting of undesired residue, in particular in liquid form, such as blood or any solution injected into the extraction location prior to liposuction to facilitate extraction of adipose tissue.

The vessel (4) of the separating unit (B) of said embodiment comprises a first inlet opening, for receiving extracted adipose tissue from the liposuction device. The inlet opening being located within the retentate volume of the vessel and being fluidly connected to the outlet of the liposuction cannula by a liposuction tube (3a). The example separating unit (B) also includes a second, feeding opening for feeding a portion of the adipose tissue stored in the retentate volume of the vessel. The feeding opening is fluidly connected to the re-injection pump (5b) and to the lipofilling device by a feeding tube (3b, 3c), and in some examples, via a three way valve (3v). Both inlet opening and feeding opening are located in the retentate volume of the vessel, for example on the lid sealingly coupled to the beaker. The example separating unit (B) also includes a third, discharge opening (4o) located at the lowest point of the filtrate volume of the vessel (4) when in use, for discharging any excess material therefrom. Discharge can be driven by gravity only by simply opening a valve (4v) or it can be driven by connecting said opening to a vacuum pump, advantageously to the vacuum pump (5a) used to drive the liposuction operation. In some examples, the separation means includes the discharge opening (4o) allowing, after decantation or sedimentation, to eliminate the heavier fractions of the extracted adipose cells. In some examples, however, a filter is used, as it permits acceleration of the separation process by activating a vacuum pump (5a). The example separating unit (B) also includes a fourth opening for connecting the interior of the vessel to a vacuum pump (5a). As discussed above, said vacuum pump can be connected to the discharge opening. Alternatively it can be located anywhere in the vessel (4), and in some examples, in the filtrate volume in order to drive the filtration process through filter (4f), as long as it can drive the aspiration of adipose tissue out of a location of a body through the liposuction device and into the retentate volume of the vessel.

(C) Re-Injection Unit

The re-injection unit comprises a lipofilling device and a re-injection pump, both being fluidly connected to the retentate volume of the vessel (4) by tubes (3b, 3c). The lipofilling device can be powered but it is not mandatory in some examples. The cannula of a lipofilling device is usually substantially thinner than the one of a liposuction device and is often provided with a single opening for accurately injecting the selected portion of adipose cells. This is the reason why the liposuction device (10) in the apparatus of the present disclosure is not the same as the lipofilling device (100).

The re-injection pump (5b) is, in some examples, a piston pump. A piston pump is like a large syringe. It is accurate, reliable, cheap, and thus disposable, which is advantageous to guarantee a sterile environment throughout the apparatus. In this respect, piston pump (5b) is normally different from the vacuum pump (5a) used for driving the lipoaspiration. The piston pump (5b) is fluidly connected to the retentate volume of the vessel (4) of the separation unit (B) by a tube (3b). The tube (3b) penetrates deep into the retentate volume of vessel (4) in order to allow aspiration of most of the selected portion of adipose tissue retained in said retentate volume. A three-way valve (3v) allows, in a first, drawing position, to draw the selected portion of adipose tissue into the reservoir of the piston pump (5b) and, in a second, feeding position, to transfer the selected portion of adipose tissue from the reservoir of the piston pump (5b) to the lumen of the cannula of the lipofilling device, and from there into a location of a body.

An example apparatus according to the present disclosure is particularly suitable for use in an example method that includes extracting adipose tissue from a location of a body with the liposuction device (10) and vacuum pump (5a) and driving the adipose tissue to the vessel (4) of the separation unit (B). The example method also includes separating a selected portion of adipose cells from liquids such as blood. The selected portion of adipose cells is retained in the retentate volume of the vessel. The example method also includes drawing selected portion of adipose cells from the retentate volume of the vessel (4), pressurizing said selected portion of adipose tissue, and feeding the lipofilling device with said pressurized selected portion of adipose tissue. The example method also includes re-injecting the selected portion of adipose tissue with the lipofilling device into another location of the body. The foregoing example method can be a cosmetic, liposculpture method, driven only by aesthetical considerations. Alternatively or concomitantly, the example method can be therapeutic and regenerative. For example, the selected portion of adipose tissue may comprise a concentration of Adipose Derived Stem Cell (ADSC) for stimulation of regeneration of an organ or muscle of a body.

In a liposuction-lipofilling operation, sterility of the extracted and re-injected adipose tissues is of prime importance. Considering that an apparatus for such operation comprises numerous elongated channels and lumens which are quite difficult to sterilize to a high degree with sterilization units usually available to medical practices active in such operation (usually thermal units), it is safer that each element of the kit of parts and apparatus entering in contact with adipose tissue, be sterilized in plant in optimized conditions and supplied to the medical practices in sealed packages, unpacked before use, used and disposed of after the operation is completed. For this reasons, in some examples, the cannula (1) of the liposuction device comprises a substantially linear, hollow, elongated body (1b) with an inner lumen extending along a longitudinal axis of symmetry, X, from A first inlet end (1i), provided with one or several openings (11) for drawing fat cells into said lumen, to a second, outlet end (1o), located at the opposite end of the elongated body, which can be coupled directly to a vacuum tube (3a), thus forming a complete sterile flowpath for the fat cells flowing from the inlet end (1i) of the cannula to the outlet of the vacuum tube and into the vessel (4).

The means for sealingly coupling the cannula outlet (1o) of the liposuction device directly to a vacuum tube (3a) may comprise any means known in the art for coupling a flexible tube to a rigid pipe. In particular, in some examples, it suffices that the portion (1bo) of the cannula downstream of the fixing means be sufficiently long to be penetrated by the flexible vacuum tube to form a gas tight contact. It is possible to use a flexible sleeve to couple, on the one hand, the outlet end (1o) of the cannula to the inlet end of the tube (3a) and, on the other hand, the upstream end of the vacuum tube (3a). This is particularly useful in case the vacuum tube, which must not collapse by the effect of the vacuum, is not flexible enough to form a gas tight contact with the cannula outlet end (1o). The outlet end portion of the cannula may comprise a circumferential groove or a circumferential flange for further securing the vacuum tube or a sleeve around the end portion of a cannula. The vacuum tube or sleeve can further be secured with a tight bridle, of the kind used by electricians. In the present context, the expressions "downstream" and "upstream" are defined with respect to the flow of fat cells during use, i.e., flowing from the cannula inlet end (1i) to the cannula outlet end (1o).

The vacuum tube and cannula can be provided to the surgeon as separate parts to be coupled together as explained above. In an alternative embodiment, the vacuum tube and cannula can be coupled in plant, e.g., by gluing or welding (3w), which saves the surgeon the trouble of connecting them. This embodiment has the advantage that the surgeon can be sure that the vacuum tube is well secured to the cannula with no risk of leak. Another advantage, is that after use, the whole system cannula+vacuum tube is disposed of, and the surgeon is not tempted to reuse the cannula for a second operation, with the risk of infection in case of incomplete sterilization of the cannula. A drawback is that the connection of the cannula+vacuum tube can be a little more cumbersome, as the downstream end of the vacuum tube may have to be inserted into the inlet end (2i) of the handpiece, all the way until the cannula fixing means (1c) reach the coupling means (2c) of the handpiece. This can be cumbersome in case the vacuum tube is long. An alternative solution is to provide the coupling means (2c) at the downstream end (2o) thererof, as illustrated in FIG. 5(b). With this geometry, the inlet end (1i) of a cannula can be inserted into the inner channel (2t) of the handpiece by its outlet end (2o) until the fixing means (1c) reach the complementary coupling means (2c) located at the rear end of the handpiece. If a vacuum tube (3a) is welded or glued to the cannula, the procedure is not changed, since the portion of the tube (1bo) downstream of the fixing means (1c) needs not penetrate into the channel. This geometry can also be advantageous in that the force with which the cannula is held inside the channel (2t) of the handpiece can be controlled. The cannula could be held very tightly, which would increase the stiffness of the cannula portion out of the channel and reduce the amplitude of orbital component or, on the contrary, it could be held loosely inside the channel (2t) to allow more flexibility in the cannula and expand the orbit's amplitude.

As illustrated in FIGS. 4-6, the handpiece is generally an elongated body extending along a longitudinal axis, X, and comprises an inner channel (2t) or lumen extending from a first, upstream end (2i) to a second, downstream end (2o). Depending on the surgeon's preferences, the handpiece may further comprise a transverse handle, similar to the handle of a pistol (not shown in the Figures). It further comprises coupling means (2c) for receiving the cannula's fixing means (1c), said coupling means (2c) being located at the upstream end (2i) or downstream end (2o) of the inner channel as illustrated in FIGS. 5(a) and (b), respectively. Traditionally, the coupling means (2c) are located at the upstream end (2i) of the handpiece, but as discussed supra, locating them at the rear of the handpiece may have advantages, such as an easier insertion of a cannula+vacuum tube integral system, the modulation of the transverse freedom of movements of the cannula at the upstream end (2i) of the handpiece, etc. The fixation means (1c) of the cannula and the complementary coupling means (2c) of the handle are such that the cannula (1) is coaxial with the inner channel of the handpiece. By "inner channel" it is meant here a lumen crossing the handpiece from an upstream end (2i) to a downsteam end (2o) and does not include a groove extending along an outer wall of the handpiece, which actually defines an "open channel". In the present invention, the flowpath of fat cells from the inlet (1i) of the cannula to the downstream end of the vacuum tube (3a) passes through the inner channel of the handpiece, without ever contacting said handpiece. This is particularly advantageous because a powered handpiece is expensive and cannot be disposed of after each operation. Sterilization requirements are therefore not as strong as if adipose tissue did contact the inner channel of the handpiece.

As illustrated in FIGS. 4(a) and 5(a) the portion (1bo) of the cannula comprised between the second, outlet end (1o) and the fixing means (1c) is preferably longer than the handpiece channel (2t) such that the second, outlet end (1o) of the cannula sticks out of the handpiece. For example, said portion can have a length of at least 10 cm, and in some examples, at least 15 cm, or in some examples, at least 20 cm.

The most expensive part of an apparatus as illustrated in FIG. 1 is the power assisted handpiece (and the CPU controlling it). The rest is only low cost elements including tubing, vessels, piston pump, and cannulas. In view of the difficulty of sterilizing in house all these low cost elements, and in view of their relatively low cost, in some examples, all such elements that enter into contact with fat cells at any stage of the operation be disposable. This way, a surgeon preparing its operation, will according to the examples disclosed herein, unwrap the various disposable components (e.g., cannulas, tubing, collecting vessel, and piston pump) from sterilized packaging, couple the various elements and handpiece together, and start vacuum drawing fat cells from one area of the body with an example liposuction device according to the present disclosure and collect them in a container (4). The example process continues with separating the fat cells from undesired body fluids by decantation or filtration and reinjecting the isolated fat cells into another part of the body with a device (e.g., the example devices disclosed herein). The example process also includes separating the handpiece of the liposuction device and, in some examples, of the reinjection device, from the cannulas and tubing, adequately disposing of the tubing (3a), piston pump (5b), cannula (1), vessel (4), re-injection cannula, and undesired body fluids, and starting the whole process again with a new patient and new disposable components.

The present disclosure therefore also provides a solution to increased safety against bacterial contamination, enhanced comfort for the surgeon, and ease of use.

EXAMPLE

A stem cells study was carried out on adipose tissue extracted with two liposuction devices: a manual liposuction device (=manual device), and a powered liposuction device as disclosed in the present disclosure (=orbital device). The parallel study involved 12 patients and looked at regenerative cell concentrations and viability analysis of a selected portion of the extracted adipose tissue consisting of stromal vascular fraction cells (SVF), collected with a manual liposuction device commonly used in practice today and with a liposuction device as defined in the present disclosure (Lipomatic 3 available from Euromi (BE)). SVF concentrations and viability after centrifugation was determined by manual hemocytometry and by Fluorated Activated Cell Sorting Flow Cytometry (FACS) looking at CD34+ cells. CD34+ cells are a mixture of stem cells, progenitors, and white blood cells of various degrees of maturity. Variables were reduced by extracting adipose tissue from a same patient with both manual and orbital devices.

The SVF separated from adipose tissue extracted with an orbital device as defined in the present disclosure yielded an average cells viability of 90% and was composed of a mean of 82 wt. % of CD34+ cells. The SVF separated from adipose tissue extracted with a manual device, on the other hand, yielded a viability of 72% only and was composed of 50 wt. % CD34+ cells. Based on hemocytometry results, it can be derived that 50 $cm^3$ of adipose tissue extracted with an orbital device contains about 276 million CD34+ cells, whilst the same volume of adipose tissue extracted with a manual device would contain 86 million CD34+ cells.

Additionally the analysis of the composition of the CD34+ cells revealed that 44% of the total population of CD34+ extracted with the orbital device were CD45+, whilst 60% of the total CD34+ population extracted with the manual device were CD45+. CD45+ is a marker for leukocytes (or white blood cells) and a low amount of CD45+ is desirable for most regenerative therapeutic applications.

These results show that the use of an orbital device as defined in the present disclosure can advantageously be used in an apparatus for extracting adipose tissue and re-injecting a selected portion of said adipose tissue with a much higher yield of viable cells, thus ensuring a permanent volume gain for cosmetic applications. They also show that for regenerative therapeutic treatments, a substantially higher yield of viable ADSC cells can be separated from a given volume of adipose tissue extracted with an orbital device. Because of the good viability of all type of cells extracted with an orbital device, the separation process of a selected portion of adipose tissue to be re-injected can be much more rapid, and the lipofilling operation can be carried out in the same session as the liposuction operation, which is unheard of to date.

The invention claimed is:

1. A kit of parts for an apparatus for liposuction and lipofilling of adipose tissue, said kit of parts comprising the following elements:
(A) an extraction unit comprising a liposuction device having:
(a) a substantially linear, hollow, elongated cannula with an inner lumen extending along a longitudinal axis, X, from a first inlet end, provided with one or several openings for drawing adipose tissue into said lumen, to a second, outlet end, located at the opposite end of the elongated body, said cannula being coupled by means of fixing means to a powered handpiece; and wherein
(b) the powered handpiece suitable for imparting a given movement to the inlet end of the cannula;
(B) a separation unit, comprising a vessel, provided with separation means, for separating in a retentate volume a selected portion of adipose tissue from liquids and other undesired solids;
(C) a re-injection unit comprising a lipofilling device comprising a cannula as defined in point (A)(a), coupled to a handpiece;
(D) a vacuum pump suitable for creating a vacuum in the lumen of the cannula of the liposuction device sufficient for drawing adipose tissue out of a location of a body;
(E) a re-injection piston pump suitable for driving said selected portion of adipose tissue from the vessel to the lumen of the cannula of the lipofilling device under sufficient pressure for injecting said selected portion of adipose tissue into a location of a body; and
(F) tubing including,
(a) a liposuction tube for bringing in fluid communication the outlet of the liposuction device cannula with a retentate volume of the vessel;
(b) a vacuum pipe for bringing in fluid communication the vessel of the separating unit to the vacuum pump, such that the vacuum pump is also in fluid communication with the inlet of the liposuction device cannula through the liposuction tube and the lumen of the cannula; and
(c) a feeding tube for bringing in fluid communication the lipofilling device with the retentate volume of the vessel and with the re-injection piston pump,
characterized in that,
the powered handpiece of the liposuction device is suitable for imparting to the inlet end of the cannula a vibrational movement comprising a first, linear component of a back and forth reciprocal movement along the longitudinal axis, X, at a frequency of 10 to 500 Hz and a second, orbital component about the longitudinal axis, X, and in that,
the kit of parts further comprises a three-way valve comprising a first connection to the feeding tube in direct fluid communication with the retentate volume of the vessel, a second connection with the feeding tube in direct fluid communication with the piston pump, and a third connection to the feeding tube in direct communication with the lipofilling device, and wherein the three way valve has a first, aspiration position, suitable for bringing the retentate volume of the vessel of the separation unit in direct fluid communication with said re-injection piston pump, and a second, injection position, suitable for bringing the re-injection piston pump in direct fluid communication with the lipofilling device.

2. The kit of parts according to claim 1, wherein the amplitude of the linear component of the vibrational movement of the inlet end of the liposuction device's cannula is not more than 10 mm.

3. The kit of parts according to claim 1, wherein the amplitude of the linear component of the vibrational movement of the inlet end of the liposuction device's cannula is between 2 and 9 mm.

4. The kit of parts according to claim 1, wherein the orbital component about the longitudinal axis, X, of the vibrational movement of the inlet end is elliptical, defined by a major diameter, D, and a minor diameter, d, the major diameter, D, being comprised between 1 and 20 mm.

5. The kit of parts according to claim 1, wherein the orbital component about the longitudinal axis, X, of the vibrational movement of the inlet end is elliptical, defined by a major diameter, D, and a minor diameter, d, the major diameter, D, being comprised between 2 and 10 mm.

6. The kit of parts according to claim 1, wherein the powered handpiece of the liposuction device is powered pneumatically.

7. The kit of parts according to claim 1, wherein:
(a) the powered handpiece comprises an inner channel extending along a longitudinal axis from a first, upstream end to a second, opposite, downstream end of the handpiece; and
(b) the fixing means of the cannula of the liposuction device is located on the elongated body between the inlet and the outlet ends, for removably and solidly fixing the cannula to the said handpiece at the level of the upstream end of the inner channel thereof, such that the portion comprised between the fixing means and the cannula outlet extends through said inner channel and such that the cannula outlet is located outside the handpiece's inner channel.

8. The kit of parts according to claim 1, wherein the vacuum pump is distinct from the re-injection pump.

9. The kit of parts according to claim 1, wherein:
(a) the separating means of the separating unit comprise a filter defining a filtrate volume of the vessel, for receiving the filtrate formed by the liquids and other undesired solids, and a retentate volume of the vessel for holding the selected portion of adipose tissue; and
(b) the vessel of the separating unit comprises a first inlet opening, for receiving extracted adipose tissue from the liposuction device, a second, feeding opening for feeding a portion of the adipose tissue stored therein, both inlet opening and feeding opening being located in the retentate volume of the vessel, a third, discharge opening located at the lowest point of the filtrate volume of the vessel when in use, for discharging any excess material therefrom, and a fourth opening for connecting the interior of the vessel to a vacuum pump.

10. Apparatus for liposuction and lipofilling of adipose tissue comprising all the elements of the kit of parts according to claim 1, wherein:
(a) the outlet of the liposuction device cannula is in fluid communication through a liposuction tube with a retentate volume of the vessel for holding the selected portion of adipose tissue after separation by the separating means said retentate volume being located within the vessel, upstream from the separating means;
(b) the vessel of the separating unit is connected through a vacuum pipe to the vacuum pump, such that the vacuum pump is also in fluid communication with the inlet of the liposuction device cannula through the liposuction tube and the lumen of the cannula;
(c) the lipofilling device is in fluid communication with the retentate volume of the vessel through a feeding tube, and with the re-injection pump, and wherein the three-way valve is connected having a first, aspiration position, wherein the retentate volume of the vessel of the separation unit for holding the selected portion of adipose tissue is in fluid communication with said piston pump, and a second, injection position, wherein the piston pump is in fluid communication with the lipofilling device, and wherein,
(d) the three-way valve is fluidly connected to the re-injection piston pump, the vessel, and the lipofilling device by means of tubing such that the re-injection piston pump is in fluid communication with the retentate volume of the vessel of the separation unit for holding the selected portion of adipose tissue when the three-way valve is in its first, aspiration position, and is in fluid communication with the lipofilling device when the three-way valve is in its second, injection position.

11. The apparatus according to claim 10 for use in a method comprising the following steps:
(a) extracting adipose tissue from a location of a body with the liposuction device and driving the adipose tissue to the vessel of the separation unit;
(b) separating a selected portion of adipose cells from liquids;
(c) drawing selected portion of adipose tissue from the vessel and feeding it under pressure to the lipofilling device; and
(d) re-injecting the selected portion of adipose tissue with the lipofilling device into a location of a body.

12. Use of an apparatus according to claim 11, wherein the liquids comprise blood.

13. Use of an apparatus according to claim 11 in a cosmetic, liposculpture method.

14. Use of an apparatus according to claim 11 in a therapeutic method wherein the selected portion of adipose tissue comprises a concentration of Adipose Derived Stem Cell (ADSC) for stimulation of regeneration of an organ or muscle of a body.

15. Use according to claim 14 in a method wherein the viability of ADSC of the selected portion of adipose tissue determined by Fluorescent Activated Cell Sorting (FACS) flow Cytometry has an average value of at least 78%.

16. Use according to claim 14 in a method wherein the viability of ADSC of the selected portion of adipose tissue determined by Fluorescent Activated Cell Sorting (FACS) flow Cytometry has an average value of at least 82%.

17. Use according to claim 14 in a method wherein the viability of ADSC of the selected portion of adipose tissue determined by Fluorescent Activated Cell Sorting (FACS) flow Cytometry has an average value of at least 85%.

18. Use according to claim 14 in a method wherein the viability of ADSC of the selected portion of adipose tissue determined by Fluorescent Activated Cell Sorting (FACS) flow Cytometry has an average value of at least 88%.

19. Use according to claim 11, wherein extraction of adipose tissue and reinjection of a selected portion of adipose tissue are carried out within a single operative session.

* * * * *